United States Patent [19]

Grob et al.

[11] Patent Number: 5,347,844
[45] Date of Patent: Sep. 20, 1994

[54] PROCESS & DEVICE FOR VAPORISATION INJECTIONS IN EQUIPMENTS FOR GAS CHROMATOGRAPHIC ANALYSIS

[75] Inventors: Konrad Grob, Fehraltorf, Switzerland; Fausto Munari, Milan, Italy

[73] Assignee: Fisons Instruments, S.P.A., Italy

[21] Appl. No.: 4,086

[22] Filed: Jan. 13, 1993

[30] Foreign Application Priority Data

Jan. 14, 1992 [IT] Italy ............................ MI92A000049

[51] Int. Cl.⁵ ............................................. G01N 30/12
[52] U.S. Cl. ................................................. 73/23.41
[58] Field of Search .......................... 73/23.41, 23.42

[56] References Cited

U.S. PATENT DOCUMENTS

| | | |
|---|---|---|
| 3,859,209 | 1/1975 | Jahnsen et al. |
| 4,704,141 | 11/1987 | Krebber ................. 73/23.41 X |
| 5,174,149 | 12/1992 | Grob et al. ............... 73/23.41 |

FOREIGN PATENT DOCUMENTS

| | | |
|---|---|---|
| 0461438A2 | 5/1991 | European Pat. Off. |
| 93100277 | 4/1993 | European Pat. Off. |
| 54-698 | 5/1979 | Japan .................. 73/23.41 |

OTHER PUBLICATIONS

Grob, "PTV Vapor Overflow—Principles of a Solvent Evaporation Technique for Introducing Large Volumes in Capillary GC", *Journal of High Resolution Chromatography*, pp. 540–546.

Grob et al., "PTV Splitless Injection of Sample Vol. up to 20 ul", *Journal of High Resolution Chromatography & Chromatography Communications*, pp. 626–632.

*Primary Examiner*—Hezron E. Williams
*Assistant Examiner*—Joseph W. Roskos
*Attorney, Agent, or Firm*—Lerner, David, Littenberg, Krumholz & Mentlik

[57] ABSTRACT

The invention concerns a process and a device for splitless vaporizing injection of samples into equipments of gas chromatographic analysis.

The technique is applied specially when liquid samples generate volumes of vapors which cannot be housed inside the vaporizing chamber.

Inside the vaporisation chamber, kept at high temperature, evaporation of the sample solvent forms a cool zone where the solutes are retained while the solvent vapors expand out of the vaporizing chamber and leave the injector. The sample liquid is kept in place within the vaporization chamber by suitable obstacles or by a packing material. At the end of solvent evaporation, i.e. when cooling ceases, the injection zone returns to the regulated injector temperature and the compounds to be analysed are transferred to the column by the carrier gas.

20 Claims, 4 Drawing Sheets

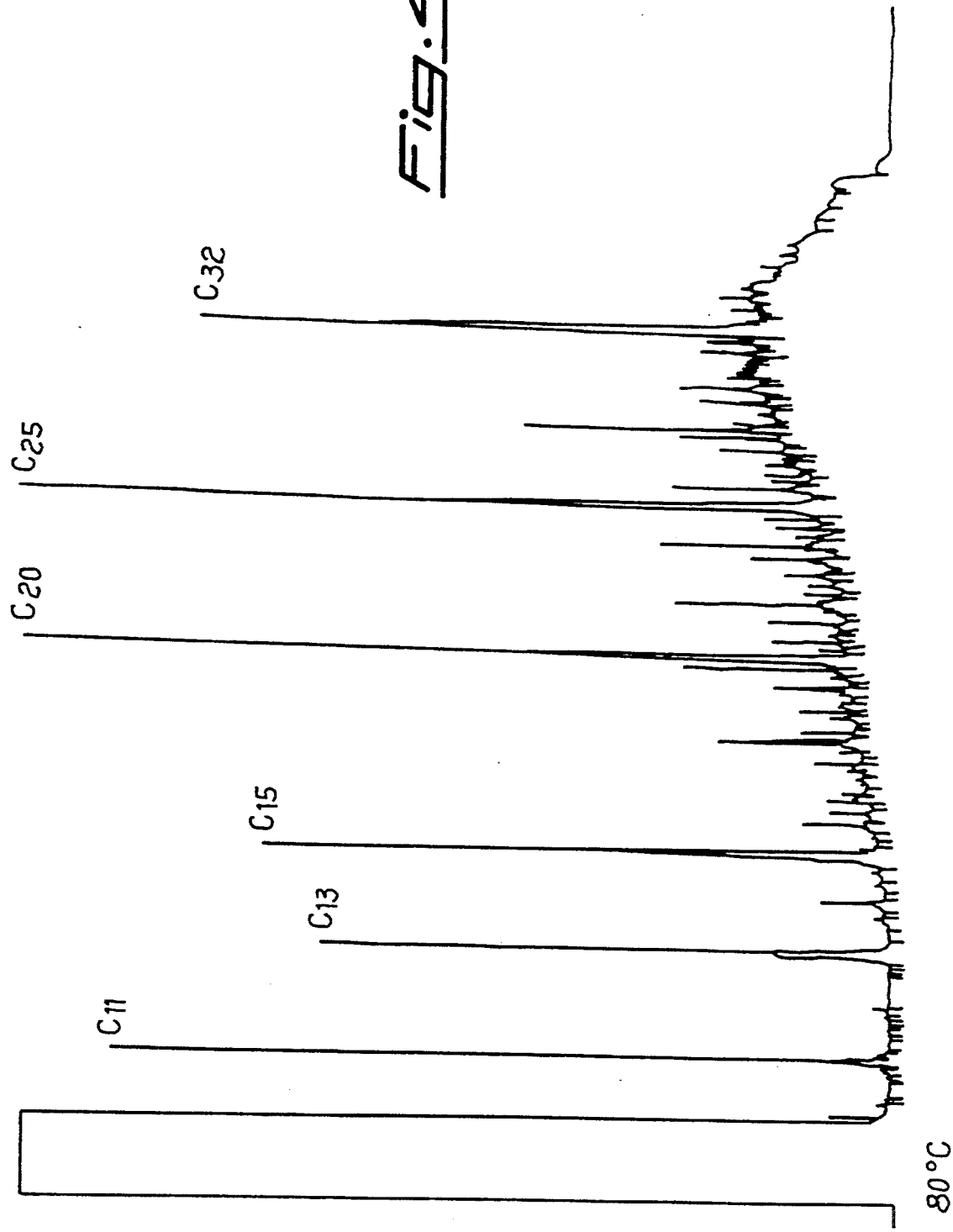

5,347,844

PROCESS & DEVICE FOR VAPORISATION INJECTIONS IN EQUIPMENTS FOR GAS CHROMATOGRAPHIC ANALYSIS

BACKGROUND OF THE INVENTION

1. Field of the Invention

The present invention relates to a process and a device for the vaporisation injection of samples in equipment for gas chromatographic analysis, in particular in absence of splitting of the compounds dissolved in the solvent, specially but not exclusively for samples having volumes exceeding 5 microliters and to be analyzed in capillary columns.

2. Description of the Prior Art

As it is well known, two main methods for sample injection in gas chromatographic analysis are presently used, well defined between one another and generally alternatively applied according to the analytical modes foreseen: vaporisation injection and non vaporising direct on column injection, the so-called "cold on-column injection".

In the vaporisation injection two different injection modes are in turn used, i.e. the split injection and the splitless one, namely in absence of splitting. The sample injection is generally performed by means of a syringe. The syringe needle injects the sample through an elastomeric membrane (septum) into a glass liner positioned inside the vaporisation chamber. In split injections, an even considerable percentage of the whole injected and vaporised sample is eliminated to the atmosphere; this kind of injection is used for relatively concentrated samples in order to avoid to introduce into the gas chromatographic column enormous amounts of sample; in the split injection glass liners filled with glass wool or a packing are commonly used.

When on the contrary the concentration of the compounds to be analysed is low, it is necessary to use the other injection mode, the splitless one, that allows to transfer into the column all the vapors of the components to be analysed in order to achieve the required sensitivity.

The conventional splitless injection takes place at a constant temperature, such as to allow the vaporisation of all sample components, and therefore at a temperature definitely higher than the solvent boiling point.

The vapors of the sample components, solvent included, are conveyed to the column during a preset time period called splitless time. During this period the sample compounds are quantitatively transferred to the column.

Once this time is over, the splitting valve is opened (located in the lower portion of the injector) and the excess of solvent, that has not been transferred into the column, is discharged to the atmosphere.

The splitless injection is usually performed by using empty glass liners. However, the use of glass liners with a glass wool cap was mentioned (Wylie et al.—Journal of High Resolution Chromatography 649–655—Vol. 14, October 1991). According to said publication, the glass wool "seems to reduce discrimination, but can give rise to active sites that catalyse the decomposition of labile molecules".

In order to avoid processes of discrimination of the heaviest components that take place in the conventional splitless injection, an injection technique with vaporisation at programmed temperature (PTV) has been developed.

By this technique the sample injection is carried out under cold conditions, at a starting temperature below the solvent boiling point and under a flow of carrier gas. Once the injection is performed, the injector body is heated in a programmed way to allow vaporisation and transfer to the column of the sample components.

It is thus possible to partially eliminate the solvent through a multi-step heating of the vaporiser (PTV solvent splitting technique). To eliminate the solvent, the vaporiser is heated to an intermediate temperature near the solvent boiling point before heating it to higher temperatures.

At this intermediate temperature the solvent is eliminated thanks to the carrier gas through the splitting valve, or in backflush, through another valve (PTV solvent splitting or PTV solvent backflushing).

The PTV solvent splitting technique was used for injection of large volumes of sample (solvents) by Vogt et al. J. Chromatogr. 174 (1979) 437 and by Termonia, Lacomblez and Munari (HRC & CC 11/1988) 890.

Another PTV injection system for the injection of larger amounts of sample is based on the solvent vaporisation by "overflow" principle, in U.S. Pat. No. 3,859,209 and more recently, with different features in EP-A 461 438. In this technique the injector (of PTV type in the recent embodiment) is packed with a suitable material and heated to a starting temperature slightly above the solvent boiling point at the working pressure. The sample injection is performed in presence or in temporary absence of carrier gas and in splitless configuration.

Under said conditions the solvent vapors escape to the atmosphere while the higher boiling components of the sample remain on the packing. After completion of solvent evaporation the vaporiser temperature is increased to allow vaporisation of said components and their passage to the chromatographic column by means of the carrier gas. During this transfer the vaporiser is kept in splitless configuration.

OBJECTS OF THE INVENTION

An object of the present invention is to provide a process and a device for vaporizing injection of large volumes of sample, wherein no temperature variation in the vaporisation system is required and the sample injection, the partial elimination of the solvent and the transfer of the sample components into the column are carried out at high temperatures, as in conventional splitless injection.

SUMMARY OF THE INVENTION

Said objects are achieved by means of the present invention that concerns a process for the injection of liquid samples into an equipment for gas chromatographic analysis, on the principle of sample vaporisation and without splitting of the compounds to be analysed, characterised by comprising the steps of:
heating the injector of said gas chromatographic equipment at a temperature of vaporisation, at least exceeding the boiling point of the solvent present in the sample to be injected at the actual pressure and sufficiently high to allow the transfer of the components to be analysed into the column;
at least temporarily connecting the vaporisation chamber of said injector with the outside by means of a duct connected to the upper part of said chamber;

temporarily creating, inside said vaporisation chamber, a cool zone having a temperature corresponding to said boiling point of the solvent, without affecting the temperature of the injector body;

injecting the sample into said vaporisation chamber at a speed such that at least part of said sample is deposited as a liquid within said cool zone;

keeping the temperature of said zone low at least until most of the solvent is evaporated;

allowing the temperature of the cool zone to return to the regulated injector temperature; and feeding the gas chromatographic column with the sample components to be analysed by means of carrier gas flow.

Said steps of formation of a cool zone, of maintenance of same and subsequent gradual heating up to the preset temperature for the injector can be performed also from the outside, for instance by introducing into the vaporisation chamber an exhaustible cold source, such as a given quantity of cryogenic agent, or by temporarily cooling the vaporisation chamber, or rather its liner, though not altering the injector body temperature. However, according to an important feature of the invention, it is particularly advantageous that said steps occur by evaporation of the sample solvent, without any intervention from the outside. One or more inert materials with a low thermal mass are needed to keep the sample liquid in place. The injected sample solvent vaporizes on said inert materials and cools the latter to the solvent boiling point without interventions from the outside, said cool zone being defined by the liquid sample itself kept in place on said inert materials. A still better cooling effect is obtained by injecting in sequence, solvent and the sample.

A solvent vaporisation with formation of a cool zone can be obtained also within the empty space of the liner, above at least one obstacle having a high thermal mass, said obstacle being impervious to liquid sample but allowing passage of the vapors thereof. When the liquid is heated from the liner and the obstacle(s) hot surfaces repel the injected sample and form it to a drop wherefrom solvent evaporates.

It is thus possible to maintain the originally set parameters of the injection system: the temperature of the cool zone selfadjusts to the actual boiling point of the solvent during the process of evaporation and elimination of the greatest part of the solvent; the compounds to be analysed are retained in the cool zone. At the end of solvent evaporation, heat transfer from the inerts returnes the temperature of the injection zone to that preset, with subsequent vaporisation of the compounds and their transfer to the column.

It has been noticed that in this way it is possible to inject even very large volumes of sample, to eliminate large part of the solvent, and to avoid complex adjustments of the parameters of the injection system. Though no thorough scientific explanation of what takes place is meant to be given herein, the localised cooling due to solvent evaporation and to the consequent localised subtraction of heat allows to retain all compounds with the exception of the most volatile ones at the evaporation site up to completion of solvent evaporation. The solvent vapors mainly flow upwards out of the vaporisation chamber, into said duct communicating with the outside. Since the carrier gas flow to the vaporisation chamber is interrupted in this step, only the solvent vapors can escape from the vaporisation chamber, mainly towards the overflow line. At the end of the solvent evaporation, the carrier gas flow is restored, the overflow line is, immediately or successively, shutted. As cooling by solvent evaporation ceases, the temperature of the vaporisation chamber returns to the injector temperature, which initializes the vaporisation of the compounds to be analysed and their transport into the column by the carrier gas flow.

Towards the end of the injection, a splitting line, preferably provided and kept closed during the previous steps, can be opened in order to free the vaporisation chamber from solvent residues as in the conventional splitless injection. As an alternative or in addition, a backflush line may allow feeding of carrier gas in countercurrent to the vaporisation chamber, to discharge the heavier compounds not to be analysed. The flow of carrier gas can be controlled by means of a valve for closing and opening the duct, that is closed before injection and opened again at the end of the solvent vaporisation, with possibility of carrier gas off take for said backflushing operation.

As an application of said process and its operating principles, a further object of the present invention is constituted by an injector for equipments of gas chromatographic analysis, of the vaporisation type, comprising: a vaporisation chamber closed by a septum and connected, on the opposite side, to a gas chromatographic column; heating means for said chamber; at least one duct to feed carrier gas to the upper part of said chamber; at least one exhaust duct towards the outside connected to the upper part of said chamber; and one or more inert packing materials, having reduced thermal mass, or liquid intercepting obstacles arranged inside said vaporisation chamber, characterised in that it comprises means to maintain the upper portion of the injector, including the septum as well as the exhaust duct, at a temperature to avoid recondensation of the solvent vapors.

According to a preferential feature of the invention, the temperature of the vaporisation chamber remains constant at a value sufficient for transferring to the gas chromatographic column the most high-boiling compound present in the sample and to be analysed.

According to another preferential feature of the invention, the inert materials are constituted by glass wool or quartz wool treated to make it inert or deactivated. Alternatively, it is possible to use a material that, besides the characteristics of thermal inertia, has an effect of chromatographic retention on the substances to be analysed, specially at the low temperatures determined by the solvent vaporisation. For example a packing may be foreseen consisting of material in granules such as poly(para-2,6-diphenylphenylene oxide) (Tenax—AKZO Registered Trademark).

Moreover, it is possible to foresee at least one liquid interception obstacle within the liner, which obstacle, when heated, maintains the sample under solvent vaporisation conditions in the liner empty space above the same.

The invention will be now described more in detail with reference to the accompanying drawings given for illustrative and non limiting purposes.

BRIEF DESCRIPTION OF THE DRAWINGS

FIG. 4 is a chromatogram of a sample of hydrocarbons injected according to the process of the invention;

DESCRIPTION OF THE PREFERRED EMBODIMENTS

Figure 1:
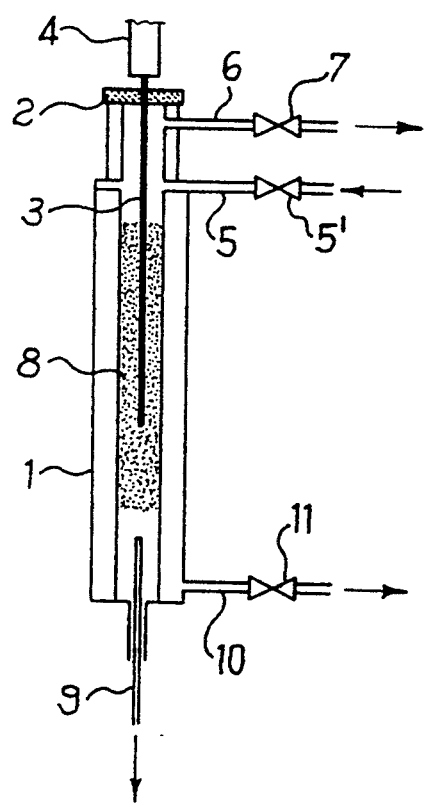
FIG. 1 is a schematic representation of an injector according to the invention in a simplified configuration.

With reference to FIG. 1, the injector according to the present invention comprises in a known way a vaporisation chamber 1, provided with heating means (not shown), a septum 2 for the introduction of the needle 3 of a syringe 4, and means to feed the chamber 1 with carrier gas, generally consisting of a duct 5 controlled by a valve 5'. Moreover, the injector comprises a further duct 6 to connect the chamber 1 with the outside, connected with the upper portion of the chamber 1 and eventually controllable by means of a valve 7, as well as one or more inert materials 8 arranged inside the chamber 1. The injector is also provided with a fitting for connection to the gas chromatographic column 9, preferably of the capillary type, as well as eventually a splitting line 10 controlled by a valve 11, whose function will be defined later on. The inerts 8, which are positioned downstream the duct 6 in respect of the carrier gas flow, have reduced thermal inertia (or thermal capacity), and/or characteristics of chromatographic retention; their presence is important in order to easily create, without external interventions, said cool zone inside the vaporisation chamber and consequently to make the injection of high volumes of sample possible without altering the composition of the sample itself.

The preferred process of the invention actually envisages to put initially the vaporisation chamber under the conditions required by the analysis, namely to heat the chamber 1 at a temperature that must at least exceed the boiling point of the solvent at the working pressure and which is preferably equivalent or higher than the temperature necessary for transferring to the column the most high-boiling compound among the compounds present in the sample to be injected and to be analysed.

As mentioned above, the adjustment of the temperature control means preferably remains constant for the whole duration of the injection. Nevertheless it is possible also to perform variations of said parameter in respect of the values originally set, being however a characteristic of the present invention the fact that these variations can be performed in a way totally independent from the injection progress.

Before performing the sample injection, the chamber 1 is put in communication with the outside by opening the valve 7 of duct 6, which has a very low fluidic resistance, while the valve 5' of carrier gas feeding and the valve 11 of the splitting duct 10 are closed. Also these conditions of communication with the outside remain unchanged until the sample is vaporised and transferred to the column 9.

At this point, with the vaporisation chamber in "steady" conditions, the sample (or a succession solvent + sample) is injected into the chamber itself in a way that at least part of the still liquid sample (or solvent) reaches the inerts 8, where it evaporates and immediately creates a cool zone allowing the realisation of the process according to the invention. It is therefore important that the first portion of sample (or solvent) injected immediately reaches the inert (glass wool, quartz wool or packing). For this purpose the injection can also be programmed, as far as its speed (high speed at the beginning) and/or position of the delivery end of the injection means (e.g. needle 3 hole) are concerned, in such a manner that the sample reaches the inert material or packing still in liquid condition.

Still in order to obtain the most favorable conditions of injection, it is preferable that the temperature of the walls of the vaporisation chamber is sufficiently high. In practice, the injector temperature selected must be such as to guarantee the transfer to the column of the most high-boiling of the compounds to be analysed present in the sample and such value is kept unchanged during the whole analysis.

When the liquid sample (or solvent) dampens the inerts 8, the solvent it contains begins to evaporate causing a localised cooling thereon. The low temperature thus reached in the points of solvent evaporation, as well as the presence of the solvent itself in liquid condition allow to hold on the inerts 8, in correspondence to the cooled zone, substantially all the compounds present in the sample.

Simultaneously, part of the evaporated solvent enters the column 9, while the greater part of the solvent vapors expand in the vaporisation chamber and is discharged therefrom to the outside through the large duct 6.

At the end of the solvent evaporation, the inerts on which said evaporation was localised, quickly get warm up to said temperature of the chamber, causing evaporation of the sample compounds which are brought to the column 9 by the reset carrier gas flow. Towards the end of the injection, the valve 11 of the splitting duct 10 can be opened to free the chamber from solvent or heavy compound residues as in the conventional splitless process.

In this way it has been found possible to perform analyses by capillary gas chromatography of samples with liquid volumes such as to generate amounts of vapors not containable inside the vaporisation chamber, particularly liquid volumes even exceeding 200 microliters. Furthermore, it is possible to use polar solvents as well, including water, in large quantities.

To carry-out the process according to the invention, the presence of a given quantity of inerts 8 or of equivalent liquid sample intercepting means is sufficient, possibly regulating the speed of sample introduction, mainly if said sample has a large volume, as a function of the surface area of the inerts themselves and/or of other working conditions.

Figure 2:
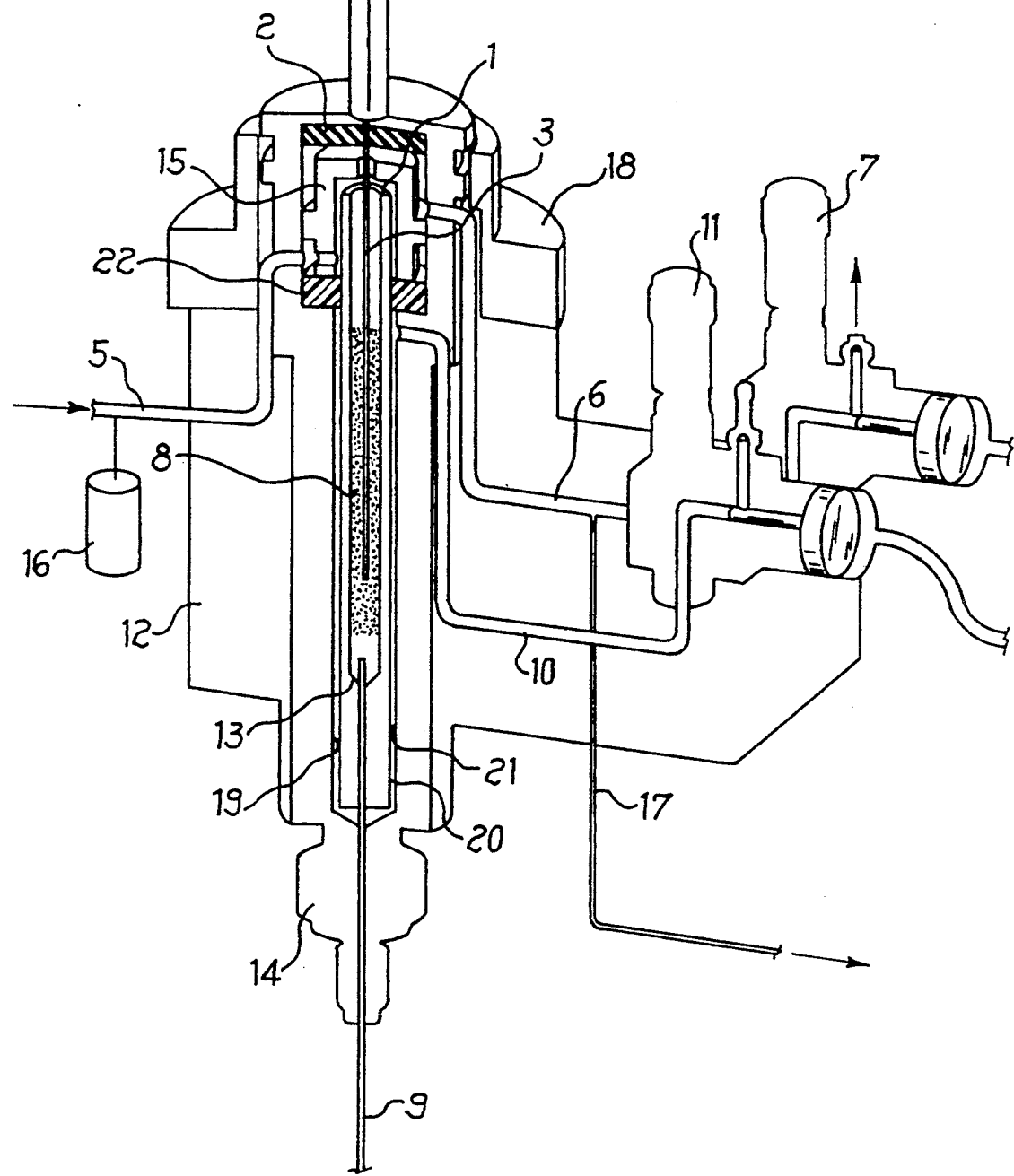
FIG. 2 is a schematic perspective section of a possible practical embodiment of an injector for the process according to the invention.

A preferential inert is constituted by a packing of poly(para-2,6-diphenylphenylene oxide) (Tenax—AKZO Registered Trademark). In order to obtain the required performances of said glass or quartz wool, this must be, as already said, inactivated, following a process that is similar to that used for the preparation of glass or fused silica capillary columns. FIG. 2 shows an operative embodiment of an injector for carrying-out the process according to the invention. Said injector comprises a body 12 of the injector, inside which there is provided a vaporisation chamber 1 defined by an external seat 19 where a calibrated is glass tube 20 (glass liner) is inserted, leaving a hollow space 21 for splitting through the duct 10, as shown later on. An upper sealing gasket 22 closes the hollow space 21. The glass liner 20 is tapered towards the bottom, as indicated by reference 13, for connection to the gas chromatographic capillary column 9, constrained by a blocking insert 14. In the upper section, the vaporisation chamber 1 presents a non tapered end that, through a small block 15 for distribution of flows and washing of the septum, known per se, comes out in correspondence to said septum 2 that can be pierced for instance by the needle 3 of a known injection syringe 4. Inside the glass liner 20 there is provided glass or quartz wool, deactivated as previously mentioned, or the packing.

It should be noted that in the present description and in the claims, "vaporisation chamber" is used to indicate in general the seat where the sample vaporisation occurs, in the illustrated example as defined by the glass liner 20. In the body 12 of the injector there are provided different ducts leading to the seat housing the liner that defines the vaporisation chamber 3. Said ducts are a duct 5 to feed carrier gas, with a control valve 5' (not shown in FIG. 2). Said duct 5 is provided with a pressure sensor 16 whose function will be described hereinbelow. Still in the body 12 of the injector, there is a duct 6 for exhausting the solvent vapors, controlled, in the vicinity of its outlet to the outside, by a valve 7, preferably a needle valve. In correspondence to a central area of said duct 6 an off take 17 can be provided consisting of a tube of small diameter that feeds a small percentage (0.5–5%) of the solvent vapors to a detector (not illustrated) for instance of the FID type. Finally, a third duct 10 defines a usual splitting line, closed by a valve 11.

Said injector is designed on the basis of a system, known per se, of split-splitless vaporisation at variable geometry, with modifications that have the purpose to guarantee: a) an appropriate elimination of the solvent vapors through the exhaust line 6 during the solvent vaporisation, avoiding the solvent condensation; and b) a monitoring of the evaporation process with indication of the end of the solvent evaporation step in order to possibly automate the injection procedure.

To achieve said objects, the exhaust line 6 must be well heated in order to avoid any condensation of the solvent therein. Said heating is obtained by means of the body 12 of the injector as well as by a special heat conducting body 18 mounted on the upper portion of the injector, the body 18 and eventually the body 12 being possibly protected towards the outside by an insulating lining (not shown). For the same reasons the valve 7 as well must be well heated at least in its portion near the duct 6. Moreover said valve must guarantee a chemical inertia not altering its characteristics because of the long lasting contact with solvent vapors and must moreover avoid the danger of fire for large quantities of solvent vapors passing there through. Therefore pneumatic valves or special electric valves are preferable.

Still in order to allow an appropriate elimination of vapors, the line 6 must be sufficiently wide (diameter 1–2 mm about) and short (30 cm or less) to obtain a very low fluidic resistance to the solvent vapors.

Moreover, in order that the process of the solvent evaporation does not affect the preset temperature of the vaporisation chamber, the quantity of conveyed heat must be such as to prevent any reduction of the selected temperature. It will therefore be necessary to guarantee the proper amount of heat depending on the selected temperature, the injected quantity, the mass of the injector, the injector speed and the speed of heat transfer to the chamber. In practice, an injector body made of aluminum is used with two heating resistors with total capacity preferably exceeding 150 W.

The monitoring of the vaporisation process can be performed through the offtake/constriction 17 on the overflow line before the exhaust valve 7.

Said off take can be connected through the gas chromatographic chamber or in another suitable way to a detector of the FID type or similar, that has the purpose of detecting when the stage of elimination of solvent vapors is over, thus allowing an appropriate timing of the process stages and their automation.

When present, said off take remains permanently open allowing in this way to eliminate the residual solvent vapors present in the overflow line when the exhaust valve is closed, as well as to maintain the septum purging. In alternative or in addition to the monitoring of the solvent through the FID, a second monitoring can be foreseen through the pressure sensor 16. In fact, during the step of the solvent vaporisation, a pressure increase inside the vaporisation chamber occurs. Said increase is recorded by the sensor. The end of the solvent vaporisation step corresponds to a recovering of the pressure initial value, that is detected by the sensor. Still with the purpose of detecting the end of the solvent vaporisation step it is possible to envisage a probe (not illustrated) that detects the temperature of the vaporisation chamber or the liner, an increase of said temperature occurring at the end of the solvent vaporisation stage.

The injector of FIG. 2 performs the process of the invention in the following way. The system is regulated at the selected temperature keeping the valve 7 open and the valves 5' (not shown in FIG. 2) and 11 closed and the sample is injected in a controlled way as indicated above. When the injected amount is great, it is preferable to carry-out a vaporisation monitoring in order to allow a choice of the switching time of the carrier gas valve 5' and of the valve 7 shutting the septum purging line. In this case the solvent evaporation is eventually monitored by means of the indicated systems (FID monitor and/or pressure sensor 16 and/or temperature probe). In absence of said systems monitoring is carried out in an experimental way. At the end of the vaporisation step, the step of the sample transfer begins, after the valve 7 is closed and the purging line is shutted. The transfer time (splitless time) is evaluated in a way similar to the process used in the conventional splitless injection, and the splitting valve 11 is opened when the most high-boiling component to be analysed has reached its step, in such a way that the total injection time is equivalent to the solvent vaporisation time plus the transfer time under splitless conditions.

Alternatively to what described above, it is possible to use a vacuum applied at the outlet of the duct 6 to accelerate the solvent vaporisation and to prevent the liquid from entering the column. In this case monitoring through the line 17 will not take place.

Still in alternative, the duct 5 of the carrier gas can be controlled by an opening/closing valve (not shown in FIG. 2). The valve is closed at the beginning of the injection and opened again towards the end of the solvent vaporisation stage, for example automatically in consequence of the monitoring of said stage, substantially in coincidence with the closure of the valve 7 on the overflow line.

FIG. 4 illustrates a chromatogram obtained by injecting a sample of 50 microliters of hydrocarbons in hexane, according to the process of the present invention.

Figure 3:
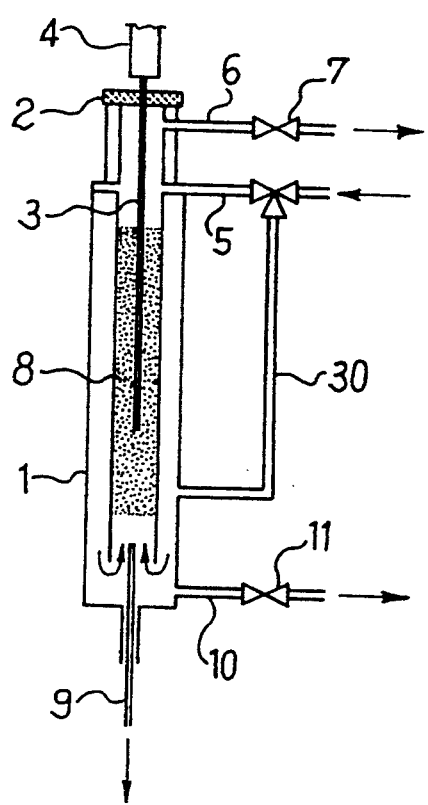
FIG. 3 is a second schematic representation of an injector according to FIG. 1 and modified for carrying-out a backflush operation after injection.
Figure 5:
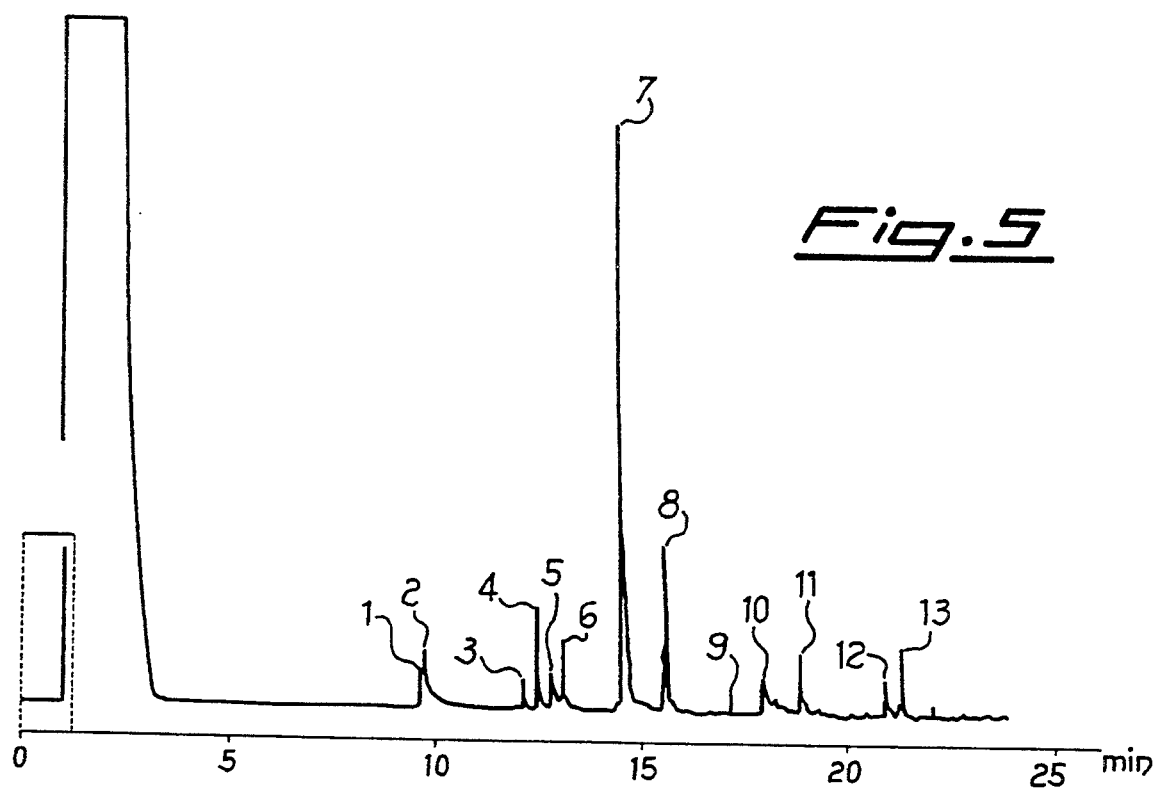
FIG. 5 is a chromatogram of a sample of phenols obtained by injecting an amount of 2 microliters according to the conventional technique.
Figure 6:
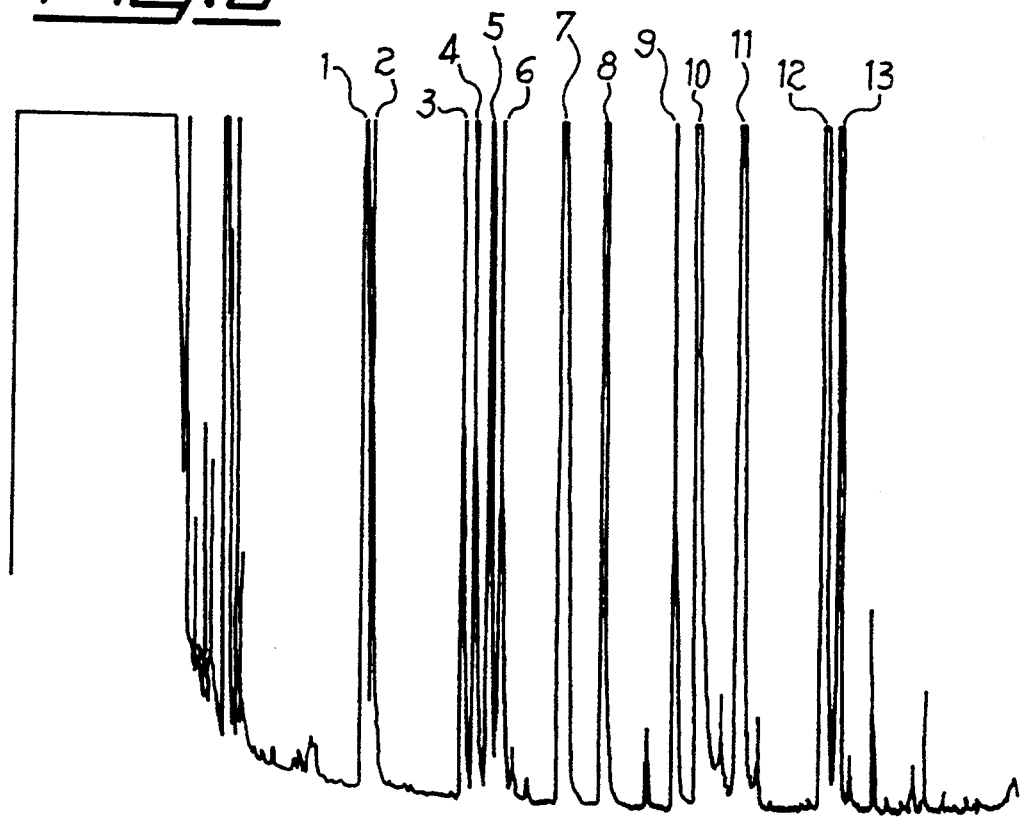
FIG. 6 is a chromatogram of the sample of FIG. 4 injected in an amount of 50 microliters according to the present invention.

FIGS. 5 and 6 are two chromatograms obtained starting from the same sample, consisting of phenols in methylene chloride, injected in 2 μl amounts according to the conventional technique and in 50 μl amounts according to the technique of the present invention respectively. In the chromatograms, reference numbers indicate:

1: phenol
2: 2-chlorophenol
3: 2-nitrophenol
4: 2,4-dimethylphenol
5: 2,4-dichlorophenol
6: naphthalene
7: 3-methyl-4-chlorophenol
8: 2,4,5-trichlorophenol
9: 2,4-dinitrophenol
10: 4-nitrophenol
11: 2-methyl-4,6-dinitrophenol
12: pentachlorophenol
13: phenanthrene Operative conditions were as follows:
splitless injection time=180 seconds (FIG. 4) and 200 seconds (FIG. 5) respectively
carrier fluid=helium
carrier flow rate=1.5 ml/min
injector temperature=350 degrees C. (FIG. 4) and 320 degrees C. (FIG. 5) respectively
detector=FID (320 degrees C.)
temperature programme of the oven=from 45 degrees C. (for 4 min) up to 270 degrees C. at 10 degrees C./min The comparison between the two chromatograms of FIGS. 4 and 5 immediately shows the ease of determination, in the second one, of compounds present in traces in the sample. FIG. 3 shows an alternative embodiment to that of FIG. 1, in which the carrier gas valve 5' can be switched to send a carrier gas flow, instead that to duct 5, to a duct 30 connected to the vaporisation chamber in such a manner that said carrier moves upwardly in countercurrent (backflushing) within the vaporisation chamber, so to wash the same and take away the heavy components not to be analysed through purge 6.

As already said, an alternative to the glass wool or packing for creating a solvent vaporisation cool zone can be obtained by means of at least one insert for instance in glass or other inert material and having a high thermal mass, said insert being fitted as a plug in the liner and being able to form an obstacle intercepting any liquid passage but allowing the passage of vapors. For instance, an insert of this type may comprise a number of little peripherical grooves forming channels with the liner wall. When the insert is heated, together with the liner wall, it repels by the Leidenfrost phenomenon the sample injected in liquid form near its upper surface. This forms a drop of liquid sample under solvent vaporisation conditions, remaining in the liner empty zone above said insert, which is consequently cooled. At the end of the solvent vaporisation step, said zone warms up and vaporizes the sample components to be analized, which are fed to the column by the carrier gas, through said insert peripherical channels. It is possible to foresee more than one insert of the above described type; moreover, a further obstacle can be provided for above the sample drop zone, this further obstacle allowing the passage also of liquid sample during the first injection step.

We claim:

1. A process for the injection of liquid samples into a gas chromatograph comprising the steps of:
maintaining an injector of said gas chromatograph, said injector including a vaporisation chamber, at a set temperature at least exceeding the boiling point, at operating pressure, of a solvent to be injected and which is sufficiently high to allow for the transfer of a component to be analyzed into a column of said gas chromatograph;
opening an exhaust duct from said vaporisation chamber;
interrupting a flow of a carrier gas through said vaporisation chamber and into said column;
temporarily creating, inside said vaporisation chamber, a cool zone having a temperature substantially equal to said boiling point of said solvent while maintaining said injector at said set temperature;
injecting said component to be analyzed into said vaporisation chamber such that at least a part of said component to be analyzed is disposed within said cool zone as a liquid;
eliminating said cool zone while maintaining said injector at said set temperature;
closing said exhaust duct and restoring said flow of carrier gas to said column;
vaporising said component to be analysed; and
transporting said vaporised component to be analyzed to said column by means of said flow of carrier gas.

2. The process according to claim 1, wherein said cool zone is formed by the evaporation of the injected solvent.

3. The process of claim 2, wherein said vaporisation chamber further comprises at least one inert packing material of low thermal mass capable of adsorbing said liquid sample when injected.

4. The process of claim 3, wherein said cooling zone is formed within said packing materials.

5. The process of claim 2, wherein said cooling zone is formed by the injection of a liquid sample including said solvent and said component to be analyzed.

6. The process of claim 2, wherein said cooling zone is formed by the injection of a solvent into said vaporisation chamber prior to the introduction of said component to be analyzed.

7. The process according to claim 1 wherein said discharged duct is only partially closed prior to said step of vaporising said component to be analysed.

8. A process according to claim 1, characterised in that the carrier gas feeding is switched off during the solvent evaporation.

9. The process according to claim 1 wherein said set temperature is sufficient to allow the transfer to the column of the most high-boiling component to be analysed.

10. The process according to claim 1, further comprising the step of backflushing the vaporisation chamber after the transfer of the component to be analysed into said column to purge the vaporisation chamber and eliminate sample residue.

11. The process according to claim 1 further comprising the step of applying a vacuum at said exhaust duct.

12. The process of claim 1, further comprising a means for hindering the passage of liquid to said column located in said vaporisation chamber, said means not impeding the flow of vapors from said vaporisation chamber.

13. The process according to claim 12 further comprising the step of manipulating the speed and/or the position of sample introduction into said vaporisation chamber as a function of the position of said obstacles, the position and amount of said packing material and/or the volume of the injected sample and type of solvent.

14. The process of claim 1 wherein said set temperature is substantially the boiling point of at least one component to be analyzed.

15. The method of claim 14 wherein said set temperature is the vaporisation temperature of the least volatile component to be analyzed.

16. A process for the injection of liquid samples including a solvent into a gas chromatograph comprising the steps of:

maintaining an injector of said gas chromatograph, said injector including a vaporisation chamber, at a set temperature at least exceeding the boiling point, at operating pressure, of said solvent to be injected and which is sufficiently high to allow for the transfer of at least one component to be analyzed within said liquid sample into a column of said gas chromatograph;

injecting said liquid sample into said vaporisation chamber in a manner such that at least a portion of said sample creates a cool zone having a temperature substantially equal to the boiling point of said solvent such that at least a portion of said sample remains in the liquid state;

vaporizing substantially all of said solvent thereby eliminating said cool zone and discharging said vaporized solvent from said vaporisation chamber through an exhaust duct thereby returning said temperature of said vaporisation chamber to said set temperature;

vaporizing said at least one component to be analyzed; and transporting said vaporized component to be analyzed to said column by means of a flow of a carrier gas.

17. The process according to claim 16, wherein said cool zone is formed by the evaporation of the injected solvent.

18. The process of claim 17, wherein said vaporisation chamber further comprises at least one inert packing material of low thermal mass capable of adsorbing said liquid sample when injected.

19. The process of claim 16 wherein said set temperature is substantially the boiling point of at least one component to be analyzed.

20. The method of claim 19 wherein said set temperature is the vaporisation temperature of the least volatile component to be analyzed.

* * * * *